(12) United States Patent
Anquez et al.

(10) Patent No.: US 12,213,832 B2
(45) Date of Patent: Feb. 4, 2025

(54) DEVICE AND METHOD FOR TREATMENT OF A PATIENT BY HIGH-INTENSITY FOCUSED ULTRASOUND (HIFU)

(71) Applicant: THERACLION SA, Malakoff (FR)

(72) Inventors: Jérémie Anquez, Paris (FR); Anthony Grisey, Saint Cyr l'Ecole (FR)

(73) Assignee: THERACLION SA, Malakoff (FR)

( * ) Notice: Subject to any disclaimer, the term of this patent is extended or adjusted under 35 U.S.C. 154(b) by 462 days.

(21) Appl. No.: 17/619,508

(22) PCT Filed: Jun. 17, 2020

(86) PCT No.: PCT/EP2020/066774
§ 371 (c)(1),
(2) Date: Dec. 15, 2021

(87) PCT Pub. No.: WO2020/254413
PCT Pub. Date: Dec. 24, 2020

(65) Prior Publication Data
US 2022/0257214 A1    Aug. 18, 2022

(30) Foreign Application Priority Data

Jun. 19, 2019 (WO) .................. PCT/IB2019/000715

(51) Int. Cl.
*A61B 8/00* (2006.01)
*A61N 7/02* (2006.01)
*A61N 7/00* (2006.01)

(52) U.S. Cl.
CPC ............ *A61B 8/4281* (2013.01); *A61B 8/485* (2013.01); *A61B 8/488* (2013.01); *A61N 7/02* (2013.01); *A61N 2007/0082* (2013.01)

(58) Field of Classification Search
CPC .... A61N 2007/0082; A61N 2007/0052; A61N 2007/0004; A61N 2007/0091; A61N 7/02; A61B 8/485; A61B 8/488; A61B 8/4281
See application file for complete search history.

(56) References Cited

U.S. PATENT DOCUMENTS

| | | |
|---|---|---|
| 8,517,943 B2 | 8/2013 | Lacoste |
| 2009/0216121 A1 | 8/2009 | Lacoste |
| 2014/0074076 A1 | 3/2014 | Gertner |
| 2017/0001043 A1* | 1/2017 | Lacoste ................ A61B 8/4461 |
| 2018/0064412 A1 | 3/2018 | Messas et al. |

FOREIGN PATENT DOCUMENTS

| | | |
|---|---|---|
| WO | 2006/129045 A2 | 12/2006 |
| WO | 2011/064209 A1 | 6/2011 |
| WO | 2019110133 A1 | 6/2019 |
| WO | 2020254413 A1 | 12/2020 |

OTHER PUBLICATIONS

International Search Report and the Written Opinion of the International Searching Authority for International Application No. PCT/EP2020/066774 mailed Aug. 10, 2020, 15 pages.

* cited by examiner

*Primary Examiner* — Gerald Johnson
(74) *Attorney, Agent, or Firm* — Finch & Maloney PLLC

(57) ABSTRACT

The invention relates to a device (1) and a method to avoid artefacts in second circulation mode imaging during ultrasound treatments of the human body (P). Specifically and amongst other effects, the invention provides a way to adequately control, in particular turn on and off, the fluid circulation (12) in a cavity (7) such as to avoid artefacts while still enabling practical imaging.

20 Claims, 4 Drawing Sheets

Figure 1:
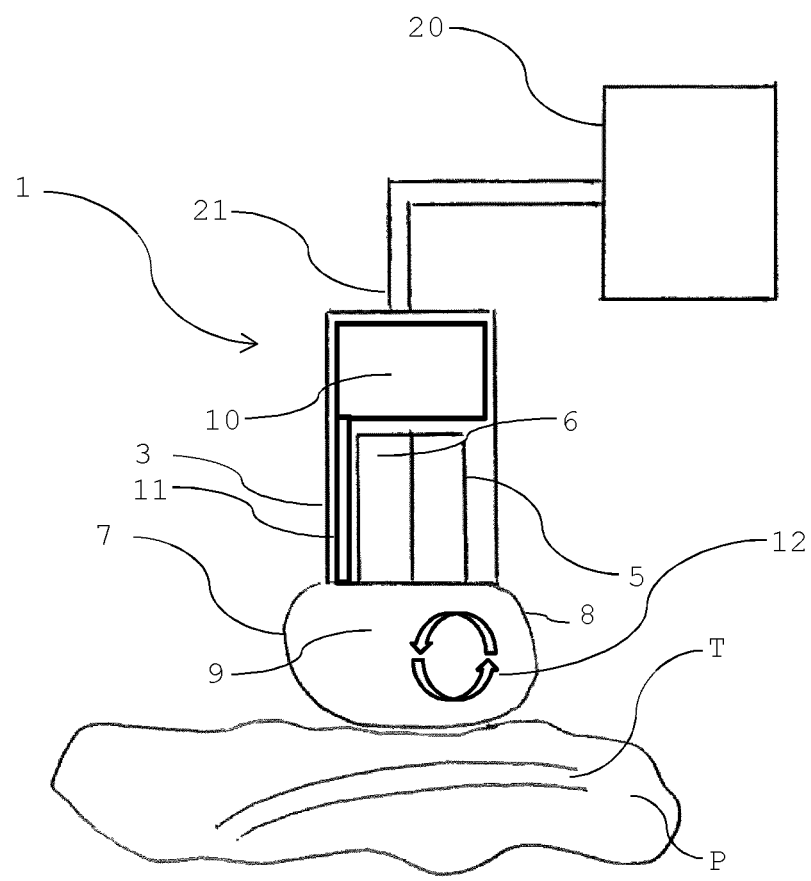

DEVICE AND METHOD FOR TREATMENT OF A PATIENT BY HIGH-INTENSITY FOCUSED ULTRASOUND (HIFU)

The invention is directed at a device and a method for treatment of a patient with High-Intensity Focused Ultrasound (HIFU) according to the independent claims.

HIFU treatments enable the non-invasive ablation of anatomical targets in the body. They are usually guided based on an imaging modality such as MRI or ultrasonography, in particular B-mode imaging.

Several devices known in the prior art have an ultrasonography imaging transducer embedded in a treatment head, which also comprises a therapy transducer, as e.g. described in WO 2006/129045. This arrangement allows for real time imaging.

To ensure acoustic coupling with the patient's anatomy, a deformable coupling balloon can be used. An example of such a deformable coupling balloon is described in WO 2011/064209.

When a HIFU device is used, the treatment head is generally placed approximately over the zone to be ablated, herein referred to as the target. Precise positioning of the focus with respect to the target is done by mechanical motion and positioning of the treatment head (e.g. if mounted on a robot) or using electronic focusing, guided by imaging provided by the associated imaging means (B-mode, MRI, . . . ). The focus represents the zone where the treatment head will deliver its energy.

Imaging means in the context of ultrasound treatments are known in the prior art. In particular, B-mode imaging is known as a method to provide a grey-scale image of the anatomy of a tissue.

Doppler imaging, on the other hand, provides information on the flow within the target tissue and/or fluid. Often, a Doppler flow map is overlaid onto a B-mode image of the anatomy. Such an overlay is typically referred to as duplex imaging.

Elastography is a known method to map elastic properties of a tissue. It is known in the art to perform elastography using ultrasonic waves, in particular for methods known as quasistatic elastography, strain imaging, acoustic radiation force impulse imaging (ARFI), shear-wave elasticity imaging (SWEI), supersonic shear imaging (SSI), and transient elastography.

In the context of the present invention, the terms "Doppler imaging", "color Doppler", and "Doppler imaging mode" shall include any imaging technique that includes information based on a Doppler technique. In particular, those terms can refer to an overlay of a color Doppler map on a B-mode image (duplex).

A fluid ensures the acoustic coupling of the treatment head to the patient's tissue. To contain the coupling fluid, the treatment head comprises a hollow space which is closed by a thin membrane, referred to as the balloon, on its distal end, i.e. the part applied to the patient.

The fluid is generally circulated by one or more pumps. The fluid pressure within the balloon can be controlled to ensure adaptation of the balloon to the patient anatomy. Temperature of the fluid can also be controlled to ensure cooling of the therapy transducer and of the patient skin.

When the treatment is guided by ultrasound imaging, color Doppler and/or elastography can be useful tools, for example to locate the target in the context of a HIFU treatment of veins.

However, the flow of liquid within the balloon induces artefacts on the Doppler image and/or elastography maps, which may render the localization of the target difficult, e.g. if the flow of blood within the target is small.

It is thus the object of the present invention to overcome the disadvantages of the prior art, in particular to provide a device and a method to treat a tissue wherein Doppler imaging can be conducted in context with HIFU treatments and in particular is not disturbed.

This and other effects are achieved by the device and the method according to the independent claims of the invention.

A device for treatment of a patient by HIFU comprises a treatment head. The treatment head includes a HIFU emitting unit, preferably a transducer, for emitting HIFU pulses. The device further includes an imaging device adapted to be operated in at least a Doppler imaging mode and/or elastography mode, and a regular imaging mode, preferably in a B-mode mode or another mode which does not comprise Doppler and/or elastographic information. The Doppler imaging mode may, in particular, be a duplex, triplex, color Doppler, or another mode comprising color Doppler information. In particular, if the imaging device comprises an imaging probe, in particular an ultrasound probe to emit and receive ultrasound waves, and a scanner adapted to process the received signal and to generate the images, the imaging probe is preferably arranged within the treatment head. The device also comprises at least a pump for circulating a fluid in a cavity between the treatment head and a contact surface of the device adapted to be brought into contact with the patient's skin. A control unit is provided for controlling operation of the imaging device and the pump. The control unit is adapted for operating the fluid circulation at least in a second circulation mode which is different from a regular circulation mode. In particular the control is adapted for starting and stopping the fluid circulation depending on the mode of operation of the imaging device.

The control unit may be adapted to operate the fluid circulation in more than these two modes, in particular it may comprise other modes for transition states between Doppler imaging mode and regular imaging mode. In particular, the control unit may be adapted for starting and stopping the fluid circulation depending on the mode of operation of the imaging device.

In particular, the invention provides a way of adequately starting and stopping the fluid circulation depending on the mode of operation of the ultrasound (US) monitoring means.

The main idea consists in stopping or reducing the fluid circulation when Doppler imaging mode and/or elastography mode is activated. This is deemed counterintuitive since it means that the cooling effect on the skin is reduced.

In a preferred embodiment, the control unit is hence adapted for switching to the second circulation mode, which comprises stopping the fluid circulation, when the Doppler imaging mode and/or elastography mode is activated. The control unit can further be adapted for switching to the regular circulation mode, which comprises switching the fluid circulation on again or increasing the flow when the Doppler imaging mode and/or elastography mode is deactivated. Thus, preferably, the second circulation mode may be a Doppler circulation mode. Alternatively, the second circulation mode may be an elastography circulation mode.

By reducing or stopping the circulation of the fluid, artefacts in the Doppler image and/or elastography maps can be avoided.

Preferably, the operation of the fluid pump is set to the second circulation mode automatically when switching the monitoring mean to Doppler imaging mode and/or elastography mode. Typically, the monitoring mean operates based on regular imaging mode, in particular in B-mode, and can be switched into a Doppler imaging mode and/or elastography mode. The fluid circulation is brought into second circulation mode when the imaging means is switched into the Doppler imaging mode and/or elastography mode. Preferably, the pumps and the pressure regulation are then brought back to the regular mode when the Doppler imaging mode and/or elastography mode is stopped and typically switched back to the regular imaging mode. Alternatively, the user interface comprises a control to switch between the second circulation mode and the regular circulation mode.

In a preferred embodiment, the treatment head includes a balloon through which said fluid can be circulated. The control is then preferably adapted to control the fluid circulation in such a way that a preset pressure is achieved within the balloon in the regular circulation mode. When the pumps are stopped, the geometry of the balloon does not adapt anymore to the patient anatomy. In particular, if some movements are performed towards or away from the patient (for example, with a robot), the fluid pressure increases or decreases, respectively. When the fluid control is set back to the regular circulation mode and the monitoring mean is switched back to the regular imaging mode, the pressure regulation is resumed. The pumps then react to deflate or inflate the balloon, respectively, in order to go back to the pressure setpoint.

In a particularly preferred embodiment, the method further comprises the step of reactivating the regular circulation mode after a delay has elapsed after sending the command to switch to the regular imaging mode.

Preferably, the control unit is adapted to reactivate the regular circulation mode after the imaging device has switched to and is operating in the regular imaging mode. In particular, the reactivation of the regular circulation mode may be based on a reception of a signal sent by the imaging device indicating that regular imaging mode is properly running.

When an echograph is set from a color Doppler imaging mode and/or elastography mode to a regular imaging mode, in particular, from duplex to B-mode, there is typically a certain time window during which the image is frozen. Thus, if the two commands ("switch to regular imaging mode" and "switch to regular circulation mode") are set simultaneously, it may happen that the balloon deflates or inflates while the live-image is frozen.

In this case, the anatomy may move while the user cannot see the movement. In the case of a treatment of veins, the vein may be barely visible in B-mode. Doppler can then be used to see it. The freezing of the image may result in the user not being able to visually follow the movement of the vein in the image when the pressure regulation is resumed.

To overcome this limitation, the two commands are preferably not sent at the same time.

In a preferred embodiment, the "switch to regular imaging mode" command is sent first, and only when the live image is available in regular imaging mode (or after a fixed delay) the "switch to regular circulation mode" command is sent. Thus, if the balloon deflates or inflates following the "switch to regular circulation mode" command, the user can visually follow the movement of the target on the live-image.

The pressure regulation can be performed with at least two pumps, wherein at least one pump acts as an inlet pump and at least one pump acts as the outlet pump Alternatively, when Doppler imaging mode and/or elastography mode is active, the pressure regulation may be temporarily resumed (with the same or different parameters as when in regular circulation mode) when certain resume conditions are reached and/or stopped again when a certain stop condition are reached. Possible resume conditions include but are not limited to (i) a movement of the treatment head is triggered along any axis, (ii) a movement of the treatment head is trigged towards or away from the patient, (iii) the measured pressure value is above or below a certain threshold relative to the current pressure setpoint (e.g. the pressure set value ±1 mBar), (iv) the geometry of the skin has deformed as assessed by an automatic detection algorithm or the user actuates a dedicated control, e.g. a button.

In case of conditions (i) or (ii), the movement itself can be triggered either at the same time, before, or after the "resume pressure regulation" command is sent.

Preferably, the control unit is adapted to change back from the temporary pressure control mode to the Second circulation mode based on a stop condition.

Possible stop conditions include, but are not limited to (i):
No movement has been triggered and/or detected along any axis since a certain pre-defined period of time, (ii) No movement has been triggered and/or detected towards or away from the patient since a certain time, (iii) the pressure is within a predetermined range around a pressure setpoint, (iv) the pressure is stable (as assessed by a moving standard deviation for example) for a certain period (e.g. 0.5 second), (v) in case where the pressure regulation is performed using two pumps, the speed of the inlet and outlet pumps, as determined by the feedback loop, are close enough from each other during a certain time, in particular for 0.1 s to 10 s, even more preferably 0.5 s to 3 s, (vi) the pressure feedback loop has been resumed for more than a certain time (e.g. 1 s), i.e. lapse of a certain time, or (vii) the user activates a dedicated input, e.g. a button.

If this solution is implemented, there should be no significant balloon inflation or deflation when leaving the second circulation mode. Thus, in this case, the commands "switch to regular imaging mode" and "switch to regular circulation mode" can either be sent simultaneously or not.

In an alternative embodiment of the invention, the circulation of the fluid is not stopped but the speed of the flow of the liquid is reduced to a "low speed level" when Doppler imaging is active. This enables to maintain the pressure regulation (although it may react more slowly) while still diminishing the induced artefacts. Alternatively, in this mode, the speed may be constant to only maintain cooling but the pressure regulation is inactive.

Preferably, the control unit is adapted for reducing the speed of the fluid to a predetermined speed. In one embodiment, the "low speed level" is fix. Alternatively, the user can set it manually based on the presence of artefacts. Preferably, the interface enables to ultimately stop the pumps if needed. Alternatively, the change into the regular mode and in particular of the speed of the flow can be set manually or automatically, based on an automatic detection of the artefacts on the Doppler image.

Preferably the switching to the "low speed level" is performed as described above in context with stopping and resuming the pressure control, in particular when switching to a Doppler imaging mode and/or elastography mode.

Alternatively, when color Doppler is activated, the "low level speed" can be stopped and started using the same stop and resume conditions, respectively, as when used to stop and start the pump.

It is of course possible for the control to be adapted to either reduce the fluid circulation or the stop it completely in second circulation mode. For example, it is conceivable that the user sets the device to either only reduce the fluid circulation or to stop it when in second circulation mode. Alternatively, the device may be adapted to adapt the second circulation mode automatically.

The invention is further directed at a method for treatment of a patient by HIFU. The method comprises the step of treating a target of the patient with HIFU pulses. In another step, a fluid is circulated in a cavity between a treatment head and a contact surface of the device adapted to be brought into contact with the patient's skin in a regular circulation mode. In another step, the target is monitored with an imaging device temporarily operating in a Doppler imaging mode and/or elastography mode, and the circulation of the fluid is changed to a Doppler imaging mode and/or elastography mode at least temporarily during monitoring in the Doppler imaging mode and/or elastography mode.

In a preferred embodiment, the method further comprises the step of switching back to the regular circulation mode, which comprises at least one of stopping or reducing the fluid circulation when Doppler imaging mode and/or elastography mode is activated, such that Doppler imaging mode and/or elastography mode is not activated unless second circulation mode is also activated.

In a particularly preferred embodiment, the method further comprises the step of switching back to the regular circulation mode, which comprises switching the circulation on again or increasing the flow when Doppler mode is deactivated, such that Doppler imaging mode and/or elastography mode is not activated unless second circulation mode is activated.

In another preferred embodiment, a device with includes a B-mode imaging device is used. The method further comprises the step of activating the B-mode imaging device when the Doppler imaging device is deactivated and the regular mode of the fluid circulation is resumed.

In another preferred embodiment, a treatment device comprising a balloon through which the fluid can be circulated is used. The method further comprises the step of controlling the fluid circulation in such a way that a preset pressure is achieved within the balloon during regular circulation mode.

In a particularly preferred embodiment, the method further comprises the step of reactivating the regular circulation mode after a delay has elapsed after sending the command to switch to the regular imaging mode.

Preferably, the control unit is adapted to reactivate the regular circulation mode after the imaging device has switched to and is operating in the regular imaging mode. In particular, the reactivation of the regular circulation mode may be based on a reception of a signal sent by the imaging device indicating that regular imaging mode is properly running.

In yet another preferred embodiment, the method further comprises the step of temporarily changing to a pressure control mode, in particular to the regular circulation mode, based on at least one of the following conditions: i.) a movement of the treatment head along any axis, in particular towards or away from the patient, ii.) the measured pressure value is above or below a certain threshold relative to the current pressure setpoint, iii) the geometry of the skin has deformed as assessed by an automatic detection algorithm, and/or iv.) a dedicated control is activated, preferably by the user.

In a preferred embodiment, the method is performed with a device comprising at least two pumps.

In a particularly preferred embodiment, the method further comprises the step of changing back from the temporary pressure control mode to the second circulation mode based on at least one of the following conditions: i.) no movement has been detected along any axis since a certain predefined period of time, in particular no movement towards or away from the patient, ii.) the pressure is within a predetermined range around the pressure setpoint iii.) the pressure is sufficiently stable, iv.) in case the pressure regulation is performed using two pumps, the speed of the inlet and outlet pumps, as determined by the feedback loop, are close enough from each other during a certain time, in particular for 0.1 s to 10 s, even more preferably 0.5 s to 3 s, v.) lapse of a certain time, and/or vi.) a dedicated input is activated, preferably by the user.

In another preferred embodiment, the method further comprises the step of reducing the speed of the fluid in the second circulation mode. Preferably, the speed of the fluid is reduced to predetermined speed. Additionally or alternatively, the speed of the fluid is reduced to a user-defined speed.

In the following, the invention is described in detail with reference to the following figures, which show:

FIG. 1 a schematic representation of a device according to the invention

FIG. 2a-2e a schematical representation of the working principle of a preferred embodiment of the invention.

Figure 3:
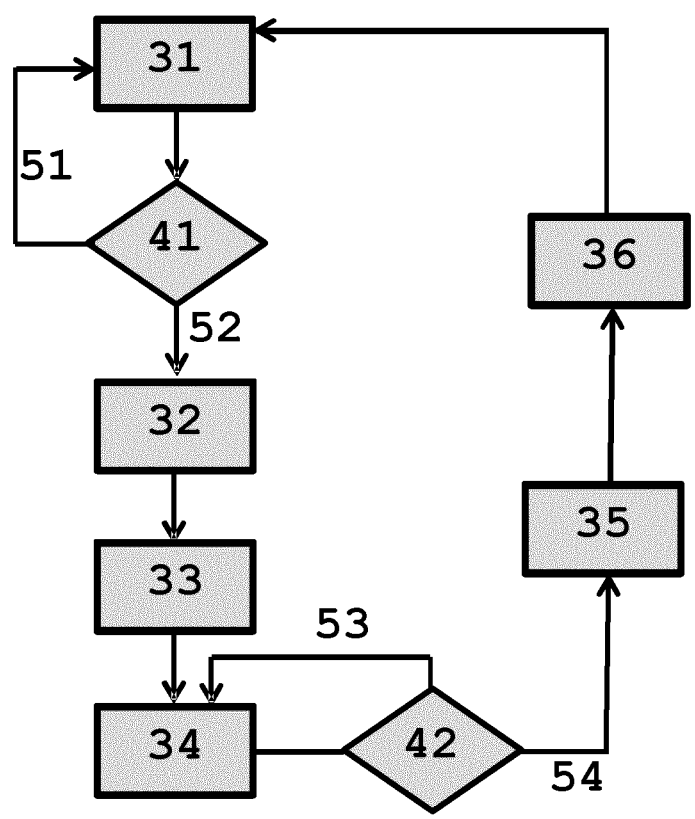
Figure 4:
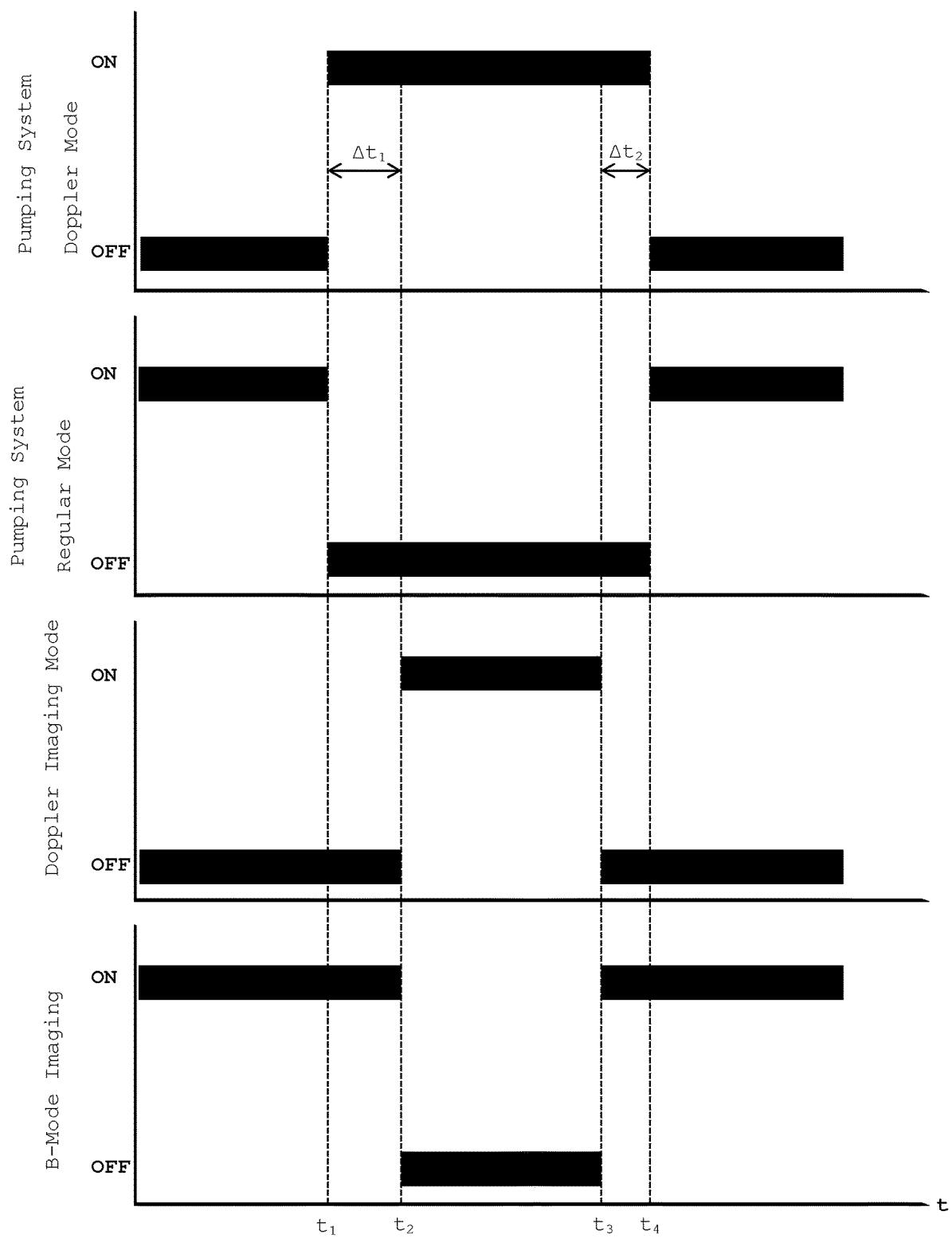

FIG. 3 a flow chart showing relevant steps of the method according to the invention FIG. 4 a schematic representation of the general idea of the invention FIG. 1 show a device 1 for treating a target T within a body part of a patient P with HIFU pulses. The device 1 comprises a treatment head 3. The treatment head 3 is provided with treatment transducer 5 and an imaging transducer 6. The treatment head is further equipped with a cavity 7 for a fluid 9, in the present embodiment in the form of a balloon 7. The balloon 7 is composed of a membrane 8 that can be filled with a fluid 9. The fluid 9 can be circulated 12 through the balloon with a pumping system 10 that is connected to the balloon 7 via an operative connection such as a pipe 11. The device further comprises a control unit 20 that is operatively connected 21 to the treatment head 3 and controls the imaging transducer 6 and the treatment transducer 5, as well as the pumping system 10.

Figures 2A, 2B, 2C, 2D, 2E:
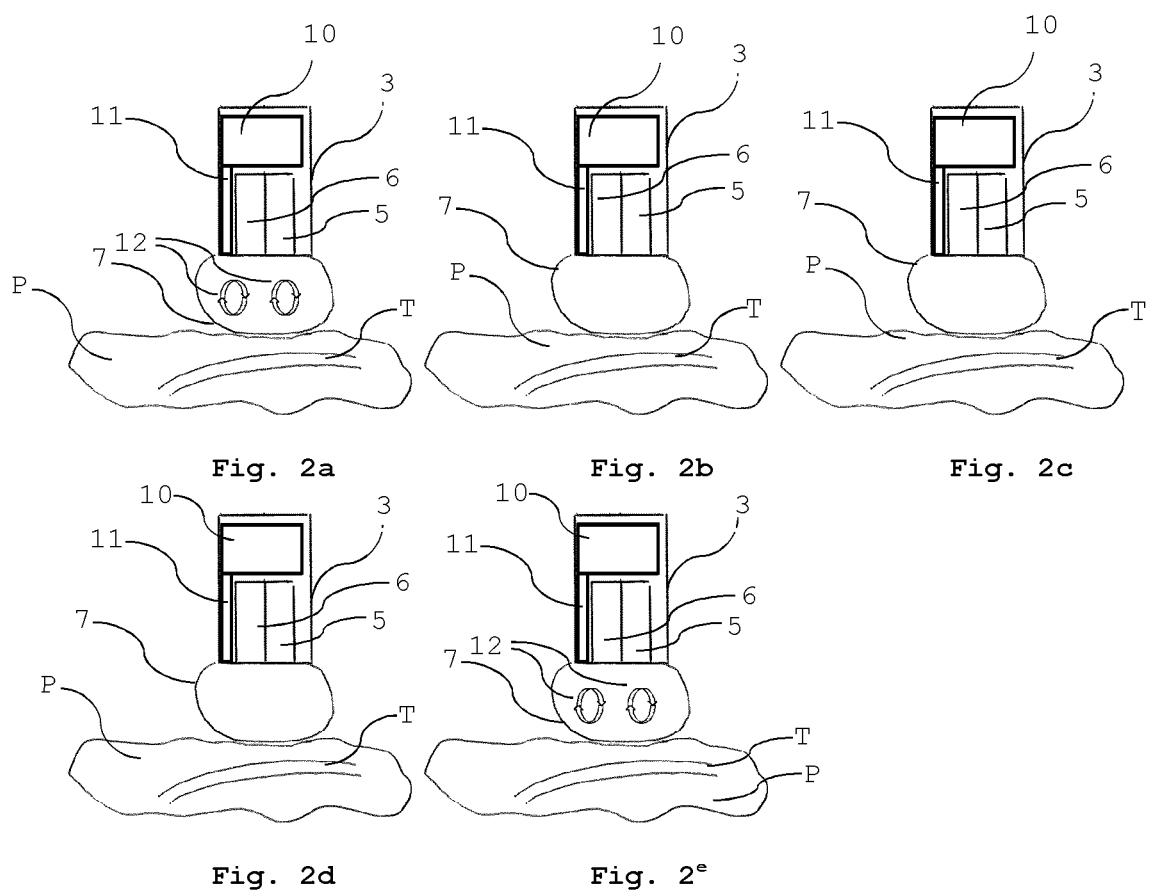

FIG. 2a shows schematically the treatment head 3 that is in contact with the skin of a patient P. The pumps 10 are activated by the control unit 20, resulting in circulation 12 of a fluid 9 within the balloon 7 mounted on the treatment head 2. In the depicted embodiment configuration in FIG. 2a, the device is run in B-mode imaging. FIG. 2b depicts an intermediary state before switching to a Doppler imaging mode and/or elastography mode, wherein the pump 10 is turned off, resulting in a stop of fluid circulation in the balloon 7. This corresponds to the second circulation mode of the pumping system, while the imaging is still conducted in B-mode. FIG. 2c depicts the treatment head after switching to Doppler imaging mode and/or elastography mode. FIG. 2d shows the intermediary state when switching back to B-mode imaging, wherein the pumping system 10 keeps the pumps turned off resulting in no circulation but switching the imaging back to B-mode. FIG. 2e shows schematically the treatment head after the pumping system 10 has turned to pump back on after B-mode imaging was resumed.

FIG. 3 shows a method according to the invention by means of a flow chart. Conventional HIFU treatment is being carried out in a treatment step 31 wherein the imaging device is operated in regular imaging mode. A trigger step 41 can be used to give the command to switch modes. As long as the trigger is not activated 51, the device images in regular imaging mode and the pumping system is in the regular circulation mode. If the operator gives the command to switch to Doppler imaging mode and/or elastography mode 52, in a first step 32, the pumping system is switched to second circulation mode. Typically, in second circulation mode, the pumping system turns off of the pumps. However, second circulation mode may also comprise slowing the pumps down instead of turning them off. Once the pumping system is in second circulation mode, the imaging device is switched to Doppler imaging mode and/or elastography mode in another step of the method 33. Once steps 32 and 33 have been carried out, the device is ready to conduct Doppler imaging without artefacts 34. Another trigger 42 can be used by the user to switch back to B-mode. As long as the trigger is not activated 53, the device remains in second circulation mode. Once the trigger is activated 54, the imaging device is first switched back to regular imaging mode in one step 35. Only once step 35 has been performed, the pumping system is switched back to regular circulation mode in another step 36 which resumes circulation of the fluid. Back in B-mode, the treatment step 31 can be resumed and, optionally, the method carried out again.

FIG. 4 shows schematically the general concept of the invention by depicting the on and off states of the pumping system modes (Doppler and Regular) and the imaging system modes (Doppler and B-mode). Initially, and as described herein, the device (1) is operating in B-mode imaging while the pumping system (10) is in regular mode. At a time $t_1$, the user may decide to switch to Doppler imaging. The control unit (20) first switches the pumping system (10) to second circulation mode, and only once second circulation mode is established, at a time $t_2$, switches to Doppler imaging mode, leading to a delay time $\Delta t_1$. Similarly, if the user gives the command to switch back to B-mode imaging at a time $t_3$, the control unit (20) first switches the imaging device (6) back to regular imaging mode, and after the imaging device (6) is generating a live image in B-mode, at a time $t_4$, switches the pumping system back to regular circulation mode. This leads to another delay time $\Delta t_2$ and ensures that the pumping system mode is never switched while in Doppler imaging mode but only in regular imaging mode, such that movement in the image due to pressure changes can be seen in B-mode.

The invention claimed is:

1. A device for treatment of a patient by High-Intensity Focus Ultrasound, the device comprising:
   a treatment head including a High-Intensity Focus Ultrasound emitting unit, for generating High-Intensity Focus Ultrasound pulses;
   an imaging device;
   a pump for circulating a fluid in a cavity between the treatment head and a contact surface of the device adapted to be brought into contact with skin of the patient;
   a control unit for controlling operation of the imaging device and the pump; and
   wherein the control unit is adapted for operating the fluid circulation at least in a second circulation mode different from a regular circulation mode, further wherein the control unit is adapted for switching to the regular circulation mode, which comprises switching the fluid circulation on again or increasing fluid flow when a Doppler imaging mode and/or an elastography mode is deactivated.

2. The device of claim 1, wherein the control unit is adapted for switching to the second circulation mode, which comprises stopping the fluid circulation, when the Doppler imaging mode and/or the elastography mode is activated.

3. The device of claim 1, wherein the treatment head includes a balloon through which said fluid can be circulated and wherein the control unit is adapted to control the fluid circulation in such a way that a preset pressure is achieved within the balloon during the regular circulation mode.

4. The device of claim 3, wherein the control unit is adapted to reactivate the regular circulation mode after a delay has elapsed after sending a command to switch to a regular imaging mode.

5. The device of claim 3, wherein the control unit is adapted to reactivate the regular circulation mode after the imaging device has switched to and is operating in a regular imaging mode.

6. The device of claim 4, where the control unit is adapted to temporarily change to a pressure control mode based on at least one of the following resume conditions:
   a movement of the treatment head along any axis;
   a measured pressure value is above or below a certain threshold relative to a current pressure setpoint;
   a geometry of the skin has deformed as assessed by an automatic detection algorithm; and
   a dedicated control is activated.

7. The device of claim 6, wherein the control unit is adapted to change back from the temporary pressure control mode to the second circulation mode based on at least one of the following conditions:
   no movement has been detected along any axis since a certain predefined period of time;
   the pressure is within a predetermined range around the pressure setpoint;
   the pressure is sufficiently stable;
   in case where pressure regulation is performed using two pumps, a speed of inlet and outlet pumps, as determined by a feedback loop, are close enough from each other during a certain time;
   lapse of a certain time; and
   a dedicated input is activated.

8. The device according to claim 1, wherein the control unit is adapted for reducing a speed of the fluid in the second circulation mode.

9. The device according to claim 8, wherein the control unit is adapted for reducing the speed of the fluid to a predetermined speed.

10. A method for treatment of a patient by High-Intensity Focused Ultrasound, the method comprising the following steps:
    treating a target of the patient with High-Intensity Focused Ultrasound pulses;
    circulating a fluid in a cavity between a treatment head and a contact surface of a device adapted to be brought into contact with skin of the patient in a regular circulation mode;
    monitoring the target with an imaging device operating temporarily in a Doppler imaging mode and/or elastography mode; and
    changing the circulation of the fluid to a second circulation mode at least temporarily during monitoring in the Doppler imaging mode.

11. The method according to claim 10, comprising the further step of switching to the second circulation mode, comprising at least one of stopping or reducing the fluid circulation, when the Doppler imaging mode is activated, such that the Doppler imaging mode is not activated unless the second circulation mode is also activated.

12. The method according to claim 10, comprising the further step of switching back to the regular circulation mode, which comprises switching the circulation on again or increasing fluid flow when the Doppler imaging mode is deactivated, such that the Doppler imaging mode and/or the elastography mode is not activated unless the second circulation mode is activated.

13. The method according to claim 12, further comprising the step of reactivating the regular circulation mode after a delay has elapsed after sending a command to switch to the regular imaging mode.

14. The method according to claim 13, further comprising the step of temporarily changing to a pressure control mode based on at least one of the following conditions:
   a movement of the treatment head along any axis;
   a measured pressure value is above or below a certain threshold relative to a current pressure setpoint;
   a geometry of the skin has deformed as assessed by an automatic detection algorithm; and
   a dedicated control is activated.

15. The method according to claim 14, further comprising the step of changing back from the temporary pressure control mode to the second circulation mode based on at least one of the following conditions:
   no movement has been detected along any axis since a certain predefined period of time;
   the pressure is within a predetermined range around the pressure setpoint;
   the pressure is sufficiently stable;
   in case where pressure regulation is performed using two pumps, a speed of inlet and outlet pumps, as determined by a feedback loop, are close enough from each other during a certain time;
   lapse of a certain time; and
   a dedicated input is activated.

16. The method according to claim 10, wherein a treatment device comprises a balloon through which the fluid can be circulated and wherein the method further comprises the step of controlling the fluid circulation in such a way that a preset pressure is achieved within the balloon during the regular circulation mode.

17. The method according to claim 10, further comprising the step of reactivating the regular circulation mode after the imaging device has switched to and is operating in the regular imaging mode.

18. The method according to claim 10, further comprising the step of reducing a speed of the fluid in the second circulation mode.

19. The method according to claim 18, wherein the speed of the fluid is reduced to a predetermined speed.

20. A device for treatment of a patient by High-Intensity Focus Ultrasound, the device comprising:
   a treatment head including a High-Intensity Focus Ultrasound emitting unit, for generating High-Intensity Focus Ultrasound pulses;
   an imaging device;
   a pump for circulating a fluid in a cavity between the treatment head and a contact surface of the device adapted to be brought into contact with skin of the patient; and
   a control unit for controlling operation of the imaging device and the pump wherein the control unit is adapted for operating the fluid circulation at least in a second circulation mode different from a regular circulation mode wherein the control unit is adapted for switching to the second circulation mode, which comprises stopping the fluid circulation, when a Doppler imaging mode and/or an elastography mode is activated.

* * * * *